(12) United States Patent
Kim et al.

(10) Patent No.: US 9,891,174 B2
(45) Date of Patent: Feb. 13, 2018

(54) REACTOR, TEST APPARATUS, AND TEST METHOD

(71) Applicant: SAMSUNG ELECTRONICS CO., LTD., Suwon-si (KR)

(72) Inventors: Kui Hyun Kim, Hwaseong-si (KR); Sang Bum Park, Hwaseong-si (KR); Joo Hee Park, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 14/985,679

(22) Filed: Dec. 31, 2015

(65) Prior Publication Data
US 2016/0187363 A1 Jun. 30, 2016

(30) Foreign Application Priority Data
Dec. 31, 2014 (KR) ........................ 10-2014-0195897

(51) Int. Cl.
| | |
|---|---|
| *G01N 15/06* | (2006.01) |
| *G01N 33/00* | (2006.01) |
| *G01N 33/48* | (2006.01) |
| *G01N 21/00* | (2006.01) |
| *G01N 21/77* | (2006.01) |

(Continued)

(52) U.S. Cl.
CPC ............ *G01N 21/77* (2013.01); *B01L 3/5027* (2013.01); *G01N 35/00069* (2013.01); *B01L 2200/0684* (2013.01); *B01L 2300/0803* (2013.01); *B01L 2300/0816* (2013.01); *B01L 2300/0864* (2013.01); *B01L 2300/0887* (2013.01); *B01L 2400/0406* (2013.01); *B01L 2400/0409* (2013.01); *G01N 21/78* (2013.01); *G01N 35/00623* (2013.01); *G01N 2021/7773* (2013.01); *G01N 2021/7783* (2013.01);
(Continued)

(58) Field of Classification Search
CPC ........ G01N 21/00; G01N 15/06; G01N 33/00; G01N 33/48
USPC ..... 422/50, 67, 68.1, 82.05; 436/43.164, 43, 436/164; 700/266; 702/1, 22, 23, 30, 31
See application file for complete search history.

(56) References Cited

U.S. PATENT DOCUMENTS

| | | | |
|---|---|---|---|
| 2002/0110488 A1* | 8/2002 | Miyake ................ | G01N 35/028 422/63 |
| 2004/0023405 A1* | 2/2004 | Bevan ................... | G01N 31/166 436/163 |

(Continued)

*Primary Examiner* — Brian J Sines
(74) *Attorney, Agent, or Firm* — Sughrue Mion, PLLC

(57) ABSTRACT

Disclosed herein are a reactor, a test apparatus, and a test method, which measure, when a material included in a sample acts as an interfering material with respect to estimating a concentration of a target material, a concentration of the interfering material, and correct an estimated concentration of the target material based on the concentration of the interfering material, thereby improving the reliability and accuracy of the concentration of the target material. The reactor includes: a target material detecting chamber in which a first reagent that includes a first material that is activated by a target material is contained; a first material detecting chamber in which a second reagent that includes the target material is contained; an inlet hole into which a sample is injected; and a channel configured to connect the inlet hole, the target material detecting chamber, and the first material detecting chamber to each other.

9 Claims, 15 Drawing Sheets

(51) Int. Cl.
*G01N 35/00* (2006.01)
*B01L 3/00* (2006.01)
*G01N 21/78* (2006.01)

(52) U.S. Cl.
CPC .............. *G01N 2035/00346* (2013.01); *G01N 2035/00851* (2013.01); *G01N 2201/121* (2013.01)

(56) References Cited

U.S. PATENT DOCUMENTS

2004/0189311 A1* 9/2004 Glezer ................. B01L 3/5027
 324/444
2007/0224084 A1* 9/2007 Holmes ................ A61B 5/1411
 422/68.1
2011/0195404 A1 8/2011 Selinfreund et al.

* cited by examiner

REACTOR, TEST APPARATUS, AND TEST METHOD

CROSS-REFERENCE TO RELATED APPLICATION

This application claims priority from Korean Patent Application No. 10-2014-0195897, filed on Dec. 31, 2014 in the Korean Intellectual Property Office, the disclosure of which is incorporated herein by reference in its entirety.

BACKGROUND

1. Field

Exemplary embodiments relate to a reactor for determining a concentration of a target material included in a sample, a test apparatus, and a test method.

2. Description of the Related Art

Lately, compact automatic equipment for analyzing a sample quickly in various fields, such as environmental monitoring, food inspection, and medical diagnosis, has been developed.

In particular, in order to measure a concentration of a target material included in a sample in the medical diagnosis field, an enzyme method of estimating a concentration of a target material by using an enzyme which is activated by the target material and an enzyme reaction in which the enzyme acts as a catalyst is used.

However, since there is a case in which a large amount of enzymes already exist in a sample or materials involved in an activation of an enzyme other than a target material exist in a sample, a method for excluding the influence of such interfering materials is needed in order to improve the reliability of an estimated concentration.

SUMMARY

Therefore, it is an aspect of one or more exemplary embodiments to provide a reactor, a test apparatus, and a test method, which measure, if a material included in a sample acts as an interfering material when estimating a concentration of a target material, a concentration of the interfering material in order to correct an estimated concentration of the target material, thereby improving the reliability and accuracy of the estimated concentration of the target material.

Additional aspects will be set forth in part in the description which follows and, in part, will be apparent from the description, or may be learned by practice of the exemplary embodiments.

In accordance with one aspect of one or more exemplary embodiments, a reactor includes: a target material detecting chamber in which a first reagent that includes a first material that is activated by a target material is contained; a first material detecting chamber in which a second reagent that includes the target material is contained; an inlet hole configured to receive an injection of a sample; and a channel configured to connect the inlet hole, the target material detecting chamber, and the first material detecting chamber to each other.

The sample may include the first material, and the first material included in the sample may be configured to act as an interfering material with respect to detecting the target material included in the sample.

Each of the first reagent and the second reagent may further include a second material that is configured for activating the first material.

The sample may include the first material and the second material, and each of the first material and the second material included in the sample may be configured to act as an interfering material with respect to detecting the target material included in the sample.

The reactor may further include a second material detecting chamber in which a third reagent that includes the target material and the first material is contained.

Each of the target material and the first material may be selected from among electrolyte ions and an enzyme.

Each of the target material, the first material, and the second material may be selected from among electrolyte ions and an enzyme.

Each of the electrolyte ions may include at least one from among a magnesium ion, a calcium ion, a potassium ion, a sodium ion, and a chlorine ion.

The enzyme may include at least one from among amylase and pyruvate kinase.

Each of the first reagent and the second reagent may further include at least one reactant that is configured to accelerate a reaction by the activated first material.

In accordance with another aspect of one or more exemplary embodiments, a test apparatus for measuring a concentration of a target material included in a sample includes: a detector configured to irradiate light of a first predetermined wavelength to a target material detecting chamber in which a first reagent that includes a first material that is activated by the target material is contained, and a first material detecting chamber in which a second reagent that includes the target material is contained, and to detect light that has propagated through or been reflected from the target material detecting chamber and the first material detecting chamber; and a controller configured to measure a concentration of the target material and a concentration of the first material based on at least one output signal provided by the detector, and to adjust the measurement of the concentration of the target material based on the measured concentration of the first material.

The test apparatus may further include a storage configured to store a factor that corresponds to a degree of influence by which the concentration of the first material included in the sample influences the measured concentration of the target material.

The controller may be further configured to measure a concentration of the target material based on a first output signal provided by the detector with respect to the target material detecting chamber, and to measure a concentration of the first material based on a second output signal provided by the detector with respect to the first material detecting chamber.

The factor may have a negative sign or a positive sign, and the controller may be further configured to adjust the measurement of the concentration of the target material by adding a value obtained by applying the factor to the measured concentration of the first material to the measured concentration of the target material.

Each of the first reagent and the second reagent may further include a second material that is configured for activating the first material, and the detector may be further configured to irradiate light of a second predetermined wavelength to a second material detecting chamber in which a third reagent that includes the target material and the first material is contained, and to detect light that has propagated through or been reflected from the second material detecting chamber.

The controller may be further configured to measure a concentration of the second material based on a third output signal provided by the detector with respect to the second material detecting chamber.

The controller may be further configured to adjust the measurement of the concentration of the target material based on the measured concentration of the first material and the measured concentration of the second material.

The test apparatus may further include a storage configured to store a first factor that corresponds to a first degree of influence by which the concentration of the first material included in the sample influences the measured concentration of the target material, and a second factor that corresponds to a second degree of influence by which the concentration of the second material influences the measured concentration of the target material.

Each of the first factor and the second factor may have a negative sign or a positive sign, and the controller may be further configured to adjust the measurement of the concentration of the target material by adding a first value obtained by applying the first factor to the measured concentration of the first material and a second value obtained by applying the second factor to the measured concentration of the second material to the measured concentration of the target material.

In accordance with still another aspect of one or more exemplary embodiments, a test method includes: measuring at least one characteristic of a first reaction product produced when a first reagent that includes a first material that is activated by a target material and at least one reactant that is configured to accelerate a reaction that involves the first material reacts with a sample that includes the target material and the first material; measuring at least one characteristic of a second reaction product produced when a second reagent that includes the target material and the at least one reactant reacts with the sample; measuring a concentration of the target material and a concentration of the first material by using the measured characteristics; and adjusting the measurement of the concentration of the target material based on the measured concentration of the first material.

The test method may further include storing a factor that corresponds to a degree of influence by which the concentration of the first material included in the sample influences the measured concentration of the target material.

The factor may have a negative sign or a positive sign, and the adjusting the measurement of the concentration of the target material may include adding a value obtained by applying the factor to the measured concentration of the first material to the measured concentration of the target material.

Each of the first reagent, the second reagent, and the sample may further include a second material that is configured for activating the first material, and the test method may further include measuring at least one optical characteristic based on a result of a reaction between a third reagent and the sample, the third reagent including the target material and the first material.

The adjusting the measurement of the concentration of the target material may include adjusting the measurement of the concentration of the target material based on the measured concentration of the first material and the measured concentration of the second material.

The test method may further include storing a first factor that corresponds to a first degree of influence by which the concentration of the first material included in the sample influences the measured concentration of the target material, and a second factor that corresponds to a second degree of influence by which the concentration of the second material included in the sample influences the measured concentration of the target material.

Each of the first factor and the second factor may have a negative sign or a positive sign, and the adjusting the measurement of concentration of the target material may include adding a first value obtained by applying the first factor to the measured concentration of the first material and a second value obtained by applying the second factor to the measured concentration of the second material to the measured concentration of the target material.

BRIEF DESCRIPTION OF THE DRAWINGS

These and/or other aspects will become apparent and more readily appreciated from the following description of exemplary embodiments, taken in conjunction with the accompanying drawings of which.

DETAILED DESCRIPTION

Figure 1:
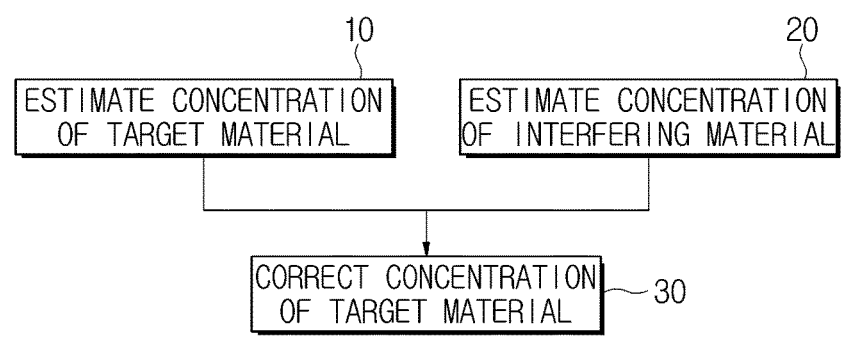
FIG. 1 is a flowchart illustrating a test method, according to an exemplary embodiment.

Reference will now be made in detail to exemplary embodiments, examples of which are illustrated in the accompanying drawings, wherein like reference numerals refer to like elements throughout.

One among various methods of estimating a concentration of a target material included in a sample is a method using an enzyme that is activated by a target material and a reaction that is catalyzed by the activated enzyme.

An example of such a method is an enzyme method for electrolyte test. According to the enzyme method, a concentration of a target material can be estimated based on a degree of activation of an enzyme. An enzyme, a composition of reagent, and a reaction mechanism can be determined based on the kind of target material. For example, an enzyme reaction using amylase which can be expressed by Reaction Formula (1) below may be used, wherein the amylase may be alpha amylase.

Reaction Formula (1)

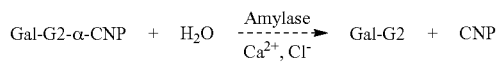

According to Reaction Formula (1), calcium ions $Ca^{2+}$ and chlorine ions $Cl^-$ activate amylase, and the activated amylase acts as a catalyst for reaction of $\alpha$-2-chloro-4-nitrophenyl-galactopyranoside (Gal-G2-$\alpha$-CNP), which is a substrate. Alternatively, oligosaccharide-CNP can be used as a substrate.

If a reaction is accelerated by the activated amylase, Gal-G2-$\alpha$-CNP is decomposed into Gal-G2 and 2-chloro-p-nitrophenol (CNP). By optically measuring color development of the CNP, a concentration of the activated amylase, a concentration of the calcium ions $Ca^{2+}$, and a concentration of the chlorine ions $Cl^-$ may be estimated.

As another example, an enzyme reaction using pyruvate kinase which can be expressed by Reaction Formula (2) below may be used.

Reaction Formula (2)

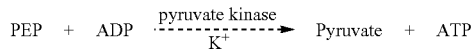

According to Reaction Formula (2), pyruvate kinase is activated by potassium ions $K^+$, and the activated pyruvate kinase acts as a catalyst for adenosine diphosphate (ADP) reaction with Phosphoenolpyruvic acid (PEP), which is a substrate. Then, pyruvate and adenosine diphosphate (ATP) are produced by a reaction between the PEP and the ADP.

Since the ATP, which is a reaction product, is involved in color development, a concentration of the potassium ions $K^+$ can be estimated by measuring the optical characteristics of the reaction product.

Since pyruvate kinase is also activated by magnesium ions $Mg^{2+}$ and sodium ions $Na^+$, magnesium ions $Mg^{2+}$ and sodium ions $Na^+$ can be used as a target material.

When a concentration of calcium ions $Ca^{2+}$ included in a sample is estimated according to Reaction Formula (1), amylase and chlorine ions $Cl^-$ may be included in a reagent that is to react with the sample. Also, when a concentration of potassium ions $K^+$ included in a sample is estimated according to Reaction Formula (2), pyruvate kinase may be included in a reagent that is to react with the sample.

Meanwhile, a human body includes calcium ions $Ca^{2+}$, amylase, chlorine ions $Cl^-$, potassium ions $K^+$, and pyruvate kinase. Accordingly, a body sample extracted from a human body may also include all of calcium ions $Ca^{2+}$, amylase, chlorine ions $Cl^-$, potassium ions $K^+$, and pyruvate kinase. If an abnormally large amount of amylase ions, chlorine ions $Cl^-$, or pyruvate kinase exists in a human body, the material acts as an interfering material, resulting in an inaccurate estimation of a concentration of calcium ions or potassium ions.

For this reason, a reactor, a test apparatus, and a test method, which can correct a measurement of a concentration of a target material when another material except for the target material acts as an interfering material with respect to a reaction, are suggested. Hereinafter, the reactor, the test apparatus, and the test method will be described in detail.

FIG. 1 is a flowchart illustrating a test method, according to an exemplary embodiment.

Referring to FIG. 1, in a test method according to an exemplary embodiment, a sample may react with a reagent to estimate a concentration of a target material, in operation 10. In order to estimate the concentration of the target material, any of various methods may be applied according to a reaction mechanism of the sample and the reagent. For example, if an enzyme method according to Reaction Formula (1) is applied, one or more optical characteristics, such as optical density or reflectance, of a reaction product produced by a reaction between a sample and a reagent may be measured, and a concentration of a target material may be estimated based on the measured optical characteristics.

Then, a concentration of an interfering material may be estimated, in operation 20. The interfering material is, as described above, a material that is used to estimate a concentration of a target material among materials included in a sample and that influences a reaction. A reaction mechanism that is used to estimate a concentration of an interfering material may be the same reaction mechanism that is used to estimate a concentration of a target material. Accordingly, by measuring the one or more optical characteristics, such as optical density or reflectance, of a reaction product produced by a reaction between a sample and a reagent, a concentration of a target material may be estimated based on the measured optical characteristics.

In this aspect, a concentration of a target material and a concentration of an interfering material may be estimated simultaneously or sequentially according to a structure of a reactor in which a sample reacts with a reagent or according to operations of a test apparatus of testing the reactor.

Then, the concentration of the target material may be corrected using the concentration of the interfering material, in operation 30. If the interfering material is included in the sample, the concentration of the target material estimated in operation 10 may have an error. Accordingly, the measurement of the concentration of the target material may be adjusted by using the concentration of the interfering material estimated in operation 20. For example, a correlation between the concentration of the target material and the concentration of the interfering material can be obtained through an experiment or simulation, and the estimated values may be applied to the correlation, thereby finally acquiring a corrected measurement of the concentration of the target material. A method of correcting a concentration of a target material, i.e., adjusting a measurement of the concentration of the target material, will be described in more detail below.

The reaction mechanisms described above may be applied to the test method according to an exemplary embodiment. Further, the test method may be applied to any case in which electrolyte ions or an enzyme existing in a human body influences a reaction, including the case of measuring a concentration of electrolyte ions or an enzyme existing in a human body using the enzyme that is activated by the electrolyte ions and a reaction that is accelerated by the activated enzyme. However, the test method can be applied to any case in which any material except for a target material among materials included in a sample acts as an interfering material to influence a reaction between the sample and a reagent.

Hereinafter, a structure of a reactor that can be used to perform the test method according to an exemplary embodiment will be described with reference to FIGS. 2, 3, 4, 5, 6, and 7.

A reactor into which a sample is injected to react with a reagent may include a cartridge reactor in which a sample or a reagent moves by a capillary force, a disk reactor in which a sample or a reagent moves by a centrifugal force, and a cuvette reactor in which measurement is performed without movement of a sample or a reagent. The structure or configuration of a test apparatus depends on the type of a reactor, and a reactor according to an exemplary embodiment may include any one of the above-mentioned types.

Figure 2:
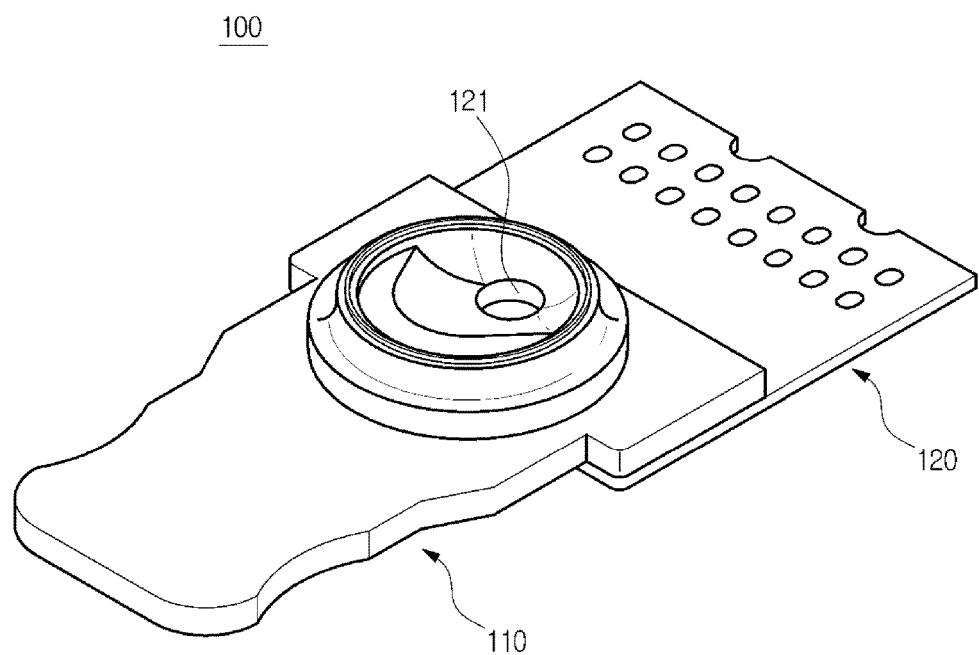
FIG. 2 shows an external appearance of a cartridge type reactor, according to an exemplary embodiment.
Figure 3:
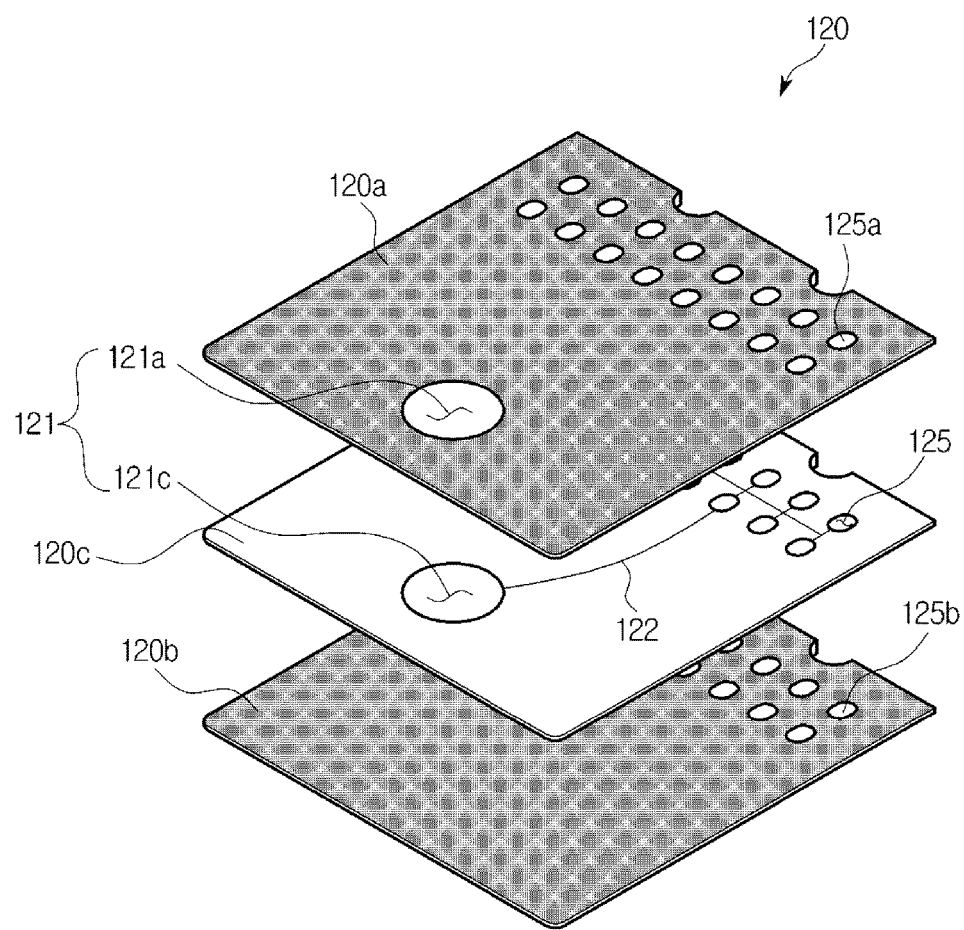
FIG. 3 is an exploded perspective view showing a structure of a platform of the reactor shown in FIG. 2.

FIG. 2 shows an external appearance of a cartridge type reactor according to an exemplary embodiment, and FIG. 3 is an exploded perspective view showing a structure of a platform of the reactor shown in FIG. 2.

Referring to FIG. 2, a reactor 100 according to an exemplary embodiment may be implemented as an analysis cartridge that includes a housing 110, and a platform 120 in which a sample reacts with a reagent.

The housing 110 may support the platform 120 while enabling a user to hold the reactor 100. The housing 110 may be made of a chemically or biologically inert material that can be easily molded.

For example, the housing 120 may be made of any of a plastic material, glass, mica, silica, a semiconductor wafer, and the like, wherein the plastic material may include any of acrylic (for example, polymethylmethacrylate (PMMA)), polysiloxane (for example, polydimethylsiloxane (PDMS)), polycarbonate (PC), polyethylene (for example, linear low density polyethylene (LLDPE), low-density polyethylene (LDPE), medium-density polyethylene (MDPE), and high-density polyethylene (HDPE)), polyvinyl alcohol, very low density polyethylene (VLDPE), polypropylene (PP), acrylonitrile-butadiene-styrene (ABS), cyclo-olefin copolymer (COC), and the like, although the housing 120 is not limited to these.

The platform 120 may be coupled with the housing 110 in such a way to be attached on the lower surface of the housing 110 or inserted into a predetermined groove 204 (see FIG. 8) formed in the housing 110.

The platform 120 may include an inlet hole 121 which is configured to receive an injection of a sample. A sample that is supplied to the reactor 100 may include a body sample such as body fluid that includes any of blood, tissue fluid, lymph fluid, urine, saliva, and marrow fluid, and a target material whose concentration is to be measured may include electrolyte ions or an enzyme existing in the sample.

The user may drop a sample to be inspected into the inlet hole 121 by using a pipette.

The sample injected into the inlet hole 121 may enter the inside of the platform 120. In the inlet hole 121, a filter may be disposed to filter the sample, which is not shown in the drawings. The filter may include a porous polymer membrane, such as any of polycarbonates (PC), polyestersulfone (PES), polyethylene (PE), polysulfone (PS), and polyarylsulfone (PASF). For example, when a blood sample is supplied, the blood sample passes through the filter so that blood cells are filtered out and only blood plasma or blood serums enter the inside of the platform 120.

Referring to FIG. 3, the platform 120 may be formed by bonding three plates. The three plates may include upper plate 120a, a lower plate 120b, and a middle plate 120c. Each of the upper plate 120a and the lower plate 120b may be coated with a light shielding ink in order to protect the sample from outside light as it moves to a plurality of chambers 125. Each of the upper plate 120a and the lower plate 120b may be formed in the form of a film, and a film that is used to form the upper plate 120a and the lower plate 120b may be selected from among a polyethylene film made of very low density polyethylene (VLDPE), linear low density polyethylene (LLDPE), low-density polyethylene (LDPE), medium-density polyethylene (MDPE), or high-density polyethylene (HDPE), a polypropylene (PP) film, a polyvinyl chloride (PVC) film, a polyvinyl alcohol (PVA) film, a polystyrene (PS) film, and a polyethylene terephthalate (PET) film.

The middle plate 120c of the platform 120 may be made of a porous sheet, such as cellulose, so as to act as a vent. The porous sheet may be made of a hydrophobic material or subject to hydrophobic processing in order to minimize its influence with respect to the movement of the sample.

In the platform 120, the inlet hole 121, a channel 122 configured to guide the movement of the sample, and the plurality of chambers 125, each chamber containing a reagent or remaining blank, may be formed. If the platform 120 has a three-layered structure as shown in FIG. 3, a upper-plate hole 121a may be formed in the upper plate 120a, and areas 125a corresponding to the chambers 125 may be transparent.

Similarly, in the lower plate 120b, areas 125b corresponding to the chambers 125 may also be transparent. When the areas 125a and 125b corresponding to the chambers 125 are transparent, a process of measuring optical characteristics based on a reaction that occurs in the chambers 125 may be optimized.

Further, in the middle plate 120c, a middle-plate hole 121c that corresponds to the inlet hole 121 may be formed. When the upper plate 120a, the middle plate 120c, and the lower plate 120b are bonded, the upper-plate hole 121a may overlap with the middle-plate hole 121c to form the inlet hole 121 of the platform 120.

In the middle plate 120c, a plurality of chambers 125 may be formed to be opposite to the middle-plate hole 121c. The chambers 125 may be formed by bonding the upper plate 120a, the middle plate 120c, and the lower plate 120b after cutting areas of the middle plate 120c corresponding to the chambers 125 into predetermined shapes, such as circles, quadrangles, etc. and removing them.

Further, in the middle plate 120c, the channel 122 may be formed to have a width that falls within a range of between 1 μm and 500 μm so that the sample injected through the inlet hole 121 can move to the chambers 125 by the capillary force of the channel 122. However, the width of the channel 122 is not limited to the range of between 1 μm and 500 μm.

A reagent to be used to detect a target material may be deposited in advance in the chambers 125 so as to be contained in respective chambers. For example, a reagent to measure a concentration of a target material may be contained in one of the chambers 125, and a reagent to measure a concentration of an interfering material may be contained in another one of the chambers 125. If two interfering materials or more exist, reagents for measuring the respective interfering materials may be respectively contained in two or more of the chambers 125.

As an example of depositing a reagent in advance in the chambers 125, there is a method of applying a reagent in a liquid state on an area 125a corresponding to a chamber of the upper plate 120a and on an area 125b corresponding to the chamber of the lower plate 120b, drying the reagent, and then bonding the upper plate 120a, the lower plate 120b, and the middle plate 120c together so that the reagent can be contained in a dried state. However, a reagent may be contained in a liquid state or in a bead state in the chambers 125.

If a sample is injected into the inlet hole 121 of the reactor 100, the sample may move to the respective chambers 125 along the channel 122. Then, the sample may react with reagents contained in the respective chambers 125 to produce reaction products, and the test apparatus 200 which will be described below may measure one or more optical characteristics of the reaction products, thereby determining estimated measurements for each of a concentration of a target material and a concentration of an interfering material.

Figure 4:
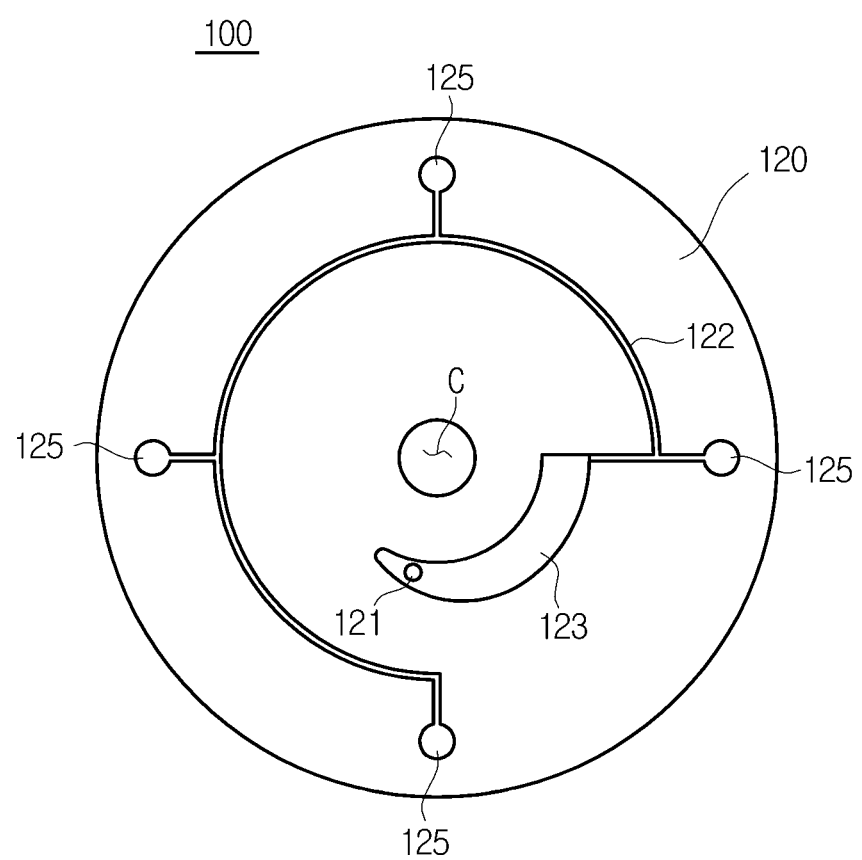
FIG. 4 shows an external appearance of a disk type reactor, according to another exemplary embodiment.

FIG. 4 shows an external appearance of a disk type reactor, according to another exemplary embodiment.

Referring to FIG. 4, a reactor 100 according to another exemplary embodiment may be implemented as a disk type reactor. In this case, the reactor 100 may be composed of a platform 120 that is rotatable, and a plurality of structures formed on the platform 120.

The structures may include a plurality of chambers 125 configured to contain samples or reagents, and a channel 122 configured to connect the chambers to each other. Although the structures are formed in the inside of the reactor 100, the structures can be seen from above, since the reactor 100 according to the current exemplary embodiment is made of a transparent material.

The platform 120 may be made of a biologically inert material that can be easily molded. The platform 120 may be made of any of a plastic material, glass, mica, silicam, a silicon wafer, and the like, wherein the plastic material may include, for example, any of polymethylmethacrylate (PMMA), polydimethylsiloxane (PDMS), polycarbonate (PC), polypropylene (PP), polyvinyl alcohol (PVA), polyethylene (PE), and the like.

However, the platform 120 may be made of any other material having chemical, biological stability and mechanical processability. Since reaction products of the reactor 100 are optically analyzed, the platform 120 has optical transparency.

The reactor 100 may move materials in a microfluidic structure by using a centrifugal force that is generated by rotation about a central region C. In the exemplary embodiment of FIG. 4, a disk type platform 120 is shown, however, the platform 120 may be formed in a fan shape or in a polygon shape, as long as it can rotate.

In the platform 120, an inlet hole 121 configured to receive an injection of a sample, a supply chamber 123 configured to contain a sample injected through the inlet hole 121 and then to supply the sample to another chamber, a plurality of chambers 125 configured to contain a reagent or to remain blank, and a channel 122 configured to guide movement of a sample from the supply chamber 123 to the chambers 125 are provided. Further, although not shown in FIG. 4, the reactor 100 may further include a structure that is configured to centrifuge blood. In order for the reactor 100 to enable stepwise reactions, a plurality of chambers may be provided in correspondence to individual steps. In addition, a reaction chamber and a detection chamber may be provided separately so that a reaction process and a detection process can be performed in different chambers.

Similarly as in the exemplary embodiment illustrated in FIG. 3, the chambers 125 of the disk type reactor 100 may also contain a reagent for detecting a target material in advance. For example, one of the chambers 125 may contain a reagent for measuring a concentration of a target material, and another one of the chambers 125 may contain a reagent for measuring a concentration of an interfering material. If two interfering materials or more exist, two or more of the chambers 125 may contain different reagents for measuring the respective interfering materials.

For example, the platform 120 may be composed of a plurality of layers of plates. If the platform 120 is composed of two plates, i.e., an upper plate and a lower plate, an engraved structure that corresponds to a microfluidic structure, such as a chamber or a channel, may be formed in the contact surfaces of the upper plate and the lower plate, and then the two plates may be bonded, thereby providing space to contain fluid and a passage to move fluid in the inside of the platform 120. The plates may be bonded by using adhesive or a double-sided adhesive tape. In addition, the plates may be bonded by using any of various methods, such as ultrasonic welding or laser welding.

As an example of depositing a reagent in advance, there is a method of applying individual reagents in a liquid state on the upper or lower plate of the platform 120, drying the reagents, and then bonding the upper plate with the lower plate so that the reagents can be contained in a dried state. However, the reagents may be contained in a liquid state or in a bead state.

In this aspect, both the reactors 100 according to the exemplary embodiments can obtain the results of a diagnosis based on a relatively small amount of sample. Further, since a sample or a reagent moves along a channel inside the reactor 100, the sample or the reagent may be in a fluid state. Accordingly, the reactors 100 are also referred to as microfluidic devices.

In the following description of exemplary embodiments, for convenience of description, the cartridge type reactor 100 as shown in FIG. 2 is used.

Figure 5:
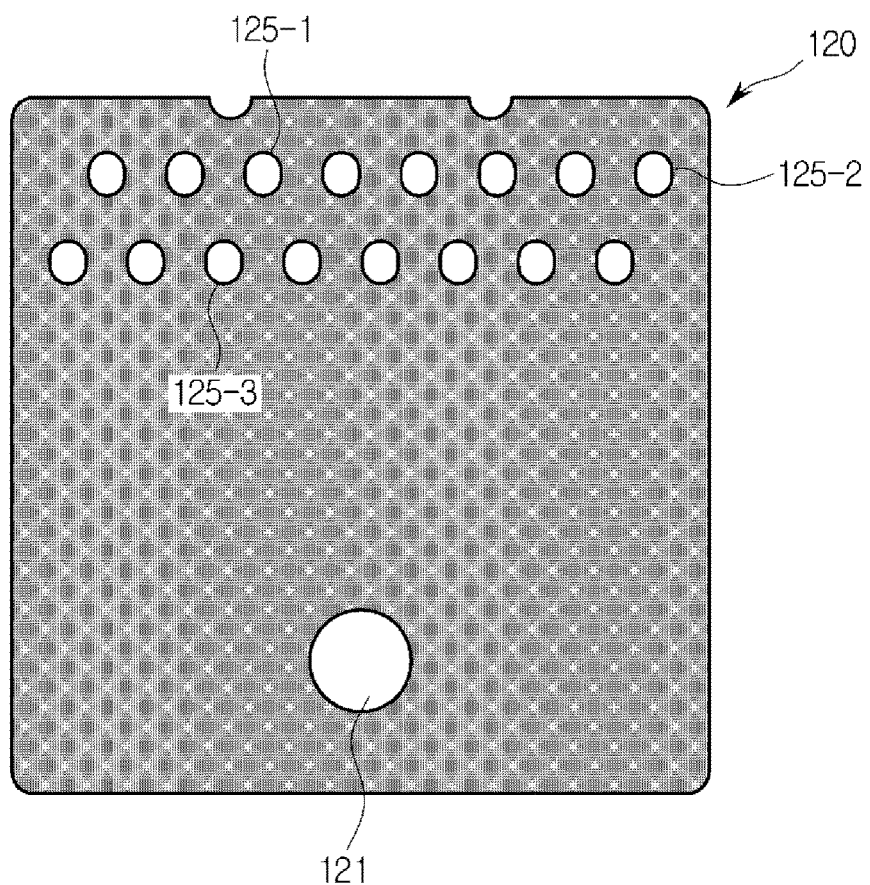
FIG. 5 is a top view of the platform of the reactor shown in FIG. 2.
Figure 6:
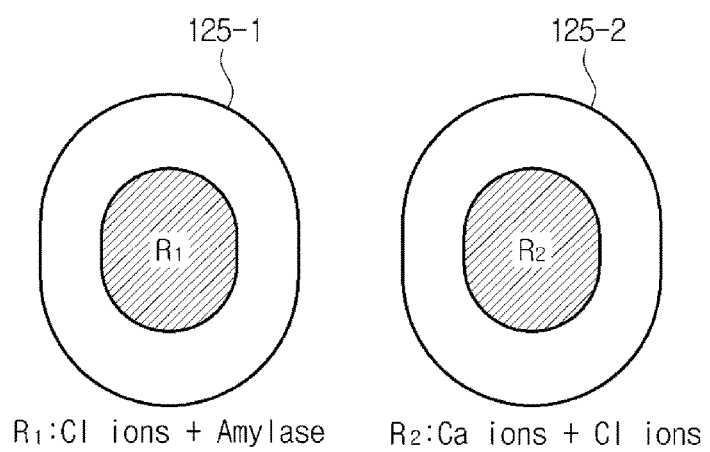
FIGS. 6 and 7 schematically show compositions of reagents that are used to measure a concentration of calcium ions using an enzyme method.
Figure 7:
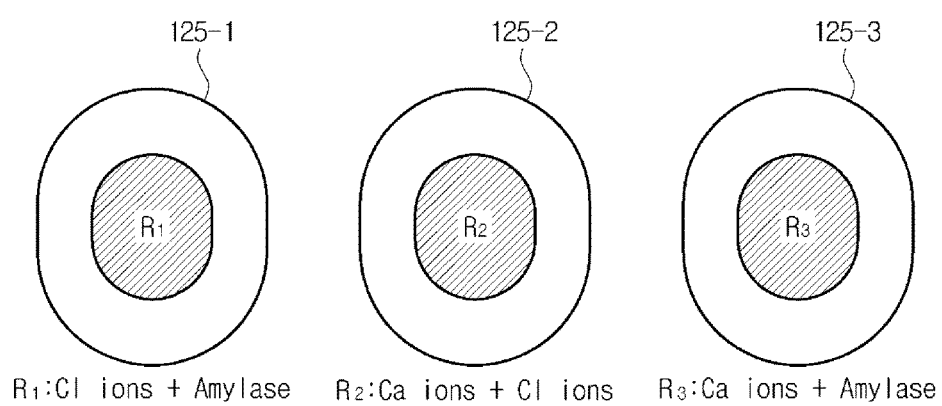

FIGS. 5, 6, and 7 are views for describing kinds of reagents that are contained in the chambers 125.

FIG. 5 is a top view of the platform 120 of the reactor 100, according to an exemplary embodiment.

As described above, the plurality of chambers 125 may be formed in the platform 120 of the reactor 100, wherein reagents may be contained in some of the chambers 125, and the remaining chambers may remain blank. Further, different kinds of reagents may be contained in the respective chambers 125 so that a plurality of items can be tested by using the single reactor 100.

In the reactor 100 according to the current exemplary embodiment, two or more chambers may be used to detect a target material. For example, referring to FIG. 5, a first reagent for detecting a target material may be contained in a chamber 125-1 among the plurality of chambers, and a second reagent for detecting an interfering material with respect to the target material may be contained in a chamber 125-2 among the remaining chambers. The chamber 125-1 in which the first reagent is contained to detect the target material is referred to as a target material detecting chamber 125-1, and the chamber 125-2 in which the second reagent is contained to detect the interfering material is referred to as an interfering material detecting chamber 125-2.

The first reagent may include a material that is activated by the target material, and at least one reactant that is configured to accelerate a reaction that involves the activated material. The second reagent may include the target material and the at least one reactant included in the first reagent.

If two kinds of interfering materials exist, a third reagent for detecting a second interfering material may be contained in yet another chamber 125-3 of the remaining chambers. In this case, the interfering materials may include a first material and a second material, and the interfering material detecting chambers may include the first material detecting chamber 125-2 and the second material detecting chamber 125-3.

In this aspect, in the current exemplary embodiment, containing the first reagent, the second reagent, or the third reagent in a chamber is not limited to the case of containing one kind of reagent in a chamber. For example, the case of containing several kinds of reagents respectively including materials included in the first reagent in the target material detecting chamber 125-1 may also correspond to the case of containing the first reagent in the target material detection chamber 125-1.

However, the configuration shown in FIG. 5 is only exemplary, and the number or locations of the chambers 125 are not limited.

FIGS. 6 and 7 schematically show compositions of reagents that are used to measure a concentration of calcium ions $Ca^{2+}$ by using the enzyme method. In FIGS. 6 and 7, a case of measuring a concentration of calcium ions $Ca^{2+}$ according to the enzyme method to which the reaction mechanism of Reaction Formula (1) is applied is shown as an example.

In the example of FIG. 6, a target material is calcium ions $Ca^{2+}$, and an interfering material is amylase. Accordingly, as shown in FIG. 6, a first reagent $R_1$ that includes chlorine ions $Cl^-$ and amylase may be contained in the target material detecting chamber 125-1, and a second reagent $R_2$ that includes calcium ions $Ca^{2+}$ and chlorine ions $Cl^-$ may be contained in the interfering material detecting chamber 125-2. Further, Gal-G2-α-CNP, which is a reactant that accelerates a reaction that involves the activated amylase, may be included in each of the first and second reagents $R_1$ and $R_2$. In addition, any one or more of buffers, surfactants, preservatives, excipients, and the like may be appropriately selected and included in the first and second reagents $R_1$ and $R_2$, as necessary.

If samples are respectively injected into the target material detecting chamber 125-1 and the interfering material detecting chamber 125-2, a reaction may occur according to Reaction Formula (1), and the test apparatus may measure the reaction optically in order to determine a concentration of calcium ions $Ca^{2+}$ and a concentration of amylase based on the results of the measurement.

FIG. 7 relates to an example for excluding the influence of chlorine ions $Cl^-$ when chlorine ions $Cl^-$ are determined as an interfering material with respect to measuring a concentration of calcium ions $Ca^{2+}$. As shown in FIG. 7, a first reagent $R_1$ that includes chlorine ions $Cl^-$ and amylase may be contained in the target material detecting chamber 125-1, a second reagent $R_2$ that includes calcium ions $Ca^{2+}$ and chlorine ions $Cl^-$ may be contained in the first material detecting chamber 125-2, and a third reagent $R_3$ that includes calcium ions $Ca^{2+}$ and amylase may be contained in the second material detecting chamber 125-3. Likewise, the first, second, and third reagents $R_1$, $R_2$, and $R_3$ may include Gal-G2-α-CNP so as to accelerate a reaction that involves activated amylase.

If samples are respectively injected into the target material detecting chamber 125-1, the first material detecting chamber 125-2, and the second material detecting chamber 125-3, a reaction may occur according to Reaction Formula (1), and the test apparatus may measure the reaction optically in order to determine a concentration of calcium ions $Ca^{2+}$, a concentration of chlorine ions $Cl^-$, and a concentration of amylase based on the results of the measurement.

In FIGS. 5, 6, and 7, examples in which the enzyme method using amylase is applied to measure a concentration of calcium ions $Ca^{2+}$ are shown; however, amylase or chlorine ions $Cl^-$ can also be a target material, since amylase and chlorine ions $Cl^-$ can also be included in clinical chemical test items.

Further, the reactors 100 according to the exemplary embodiments described above may be applied to a case of measuring a concentration of potassium ions $K^+$ by using the enzyme method using pyruvate kinase according to Reaction Formula (2), as an alternative to using the enzyme method using amylase. In this case, a first reagent may include pyruvate kinase, and a second reagent may include potassium ions $K^+$. Further, the first and second reagents may include PEP and ADP, which are reactants that accelerate a reaction that involves activated pyruvate kinase.

However, the reactors 100 according to the exemplary embodiments described above may be applied to any case in which another material than a target material included in a human body acts as an interfering material.

Hereinafter, an exemplary embodiment of a test apparatus that is configured for performing a test with respect to the reactor 100 described above will be described.

Figure 8:
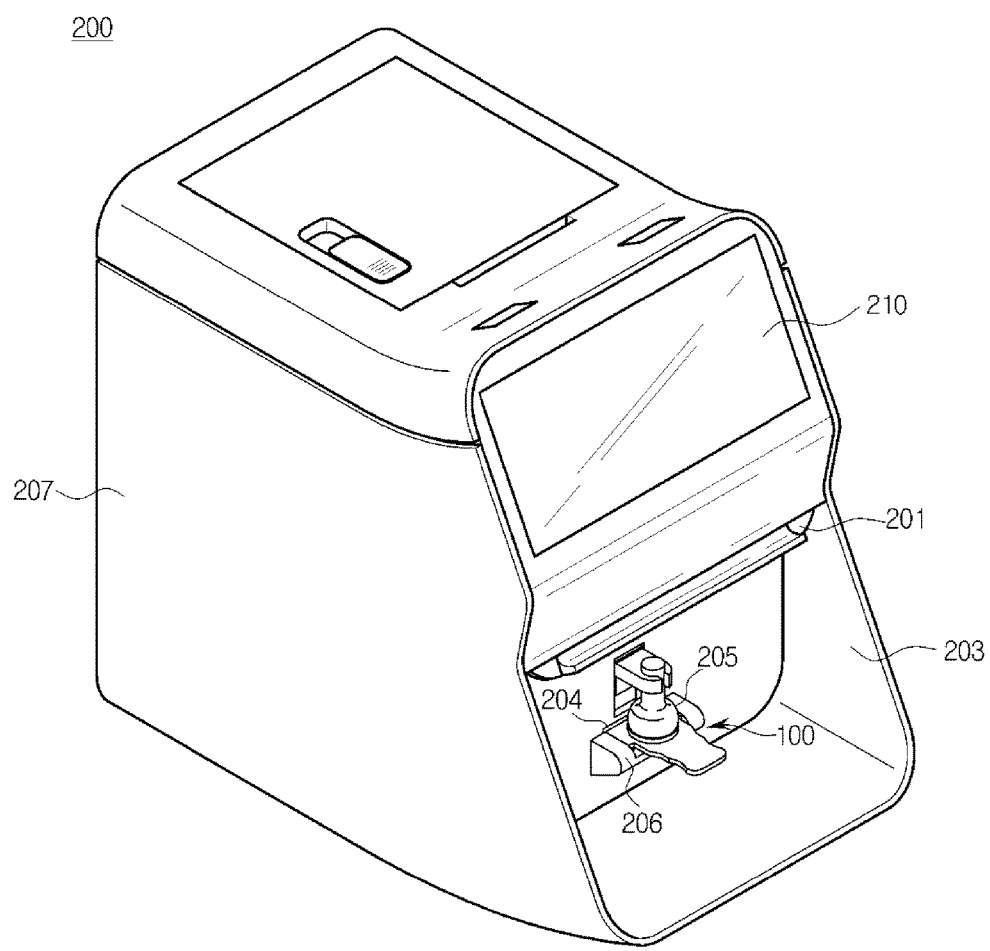
FIGS. 8 and 9 show external appearances of test apparatuses, according to exemplary embodiments.
Figure 9:
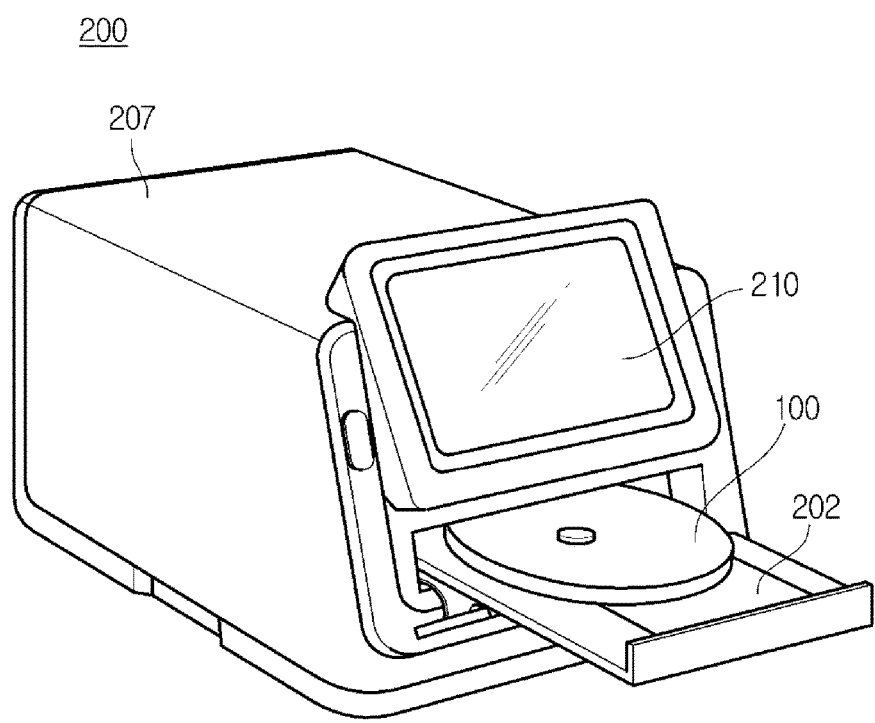

FIGS. 8 and 9 show external appearances of test apparatuses, according to exemplary embodiments.

A test apparatus 200 as shown in FIG. 8 may be used to test the cartridge type reactor 100 as shown in FIG. 2. Referring to FIG. 8, the test apparatus 100 may include an installation part 203 in which the reactor 100 is installed. A user may install the reactor 100 in the test apparatus 200 by sliding a door 201 of the installation part 203 upward to open the door 201. For example, in order to install the reactor 100 in the test apparatus 200, a user may insert the platform 120 of the reactor 100 into the predetermined groove 204 formed in the installation part 203. When the platform 120 is inserted to the inside of a main body 207, the housing 110 may be exposed outside the test apparatus 200 and supported by a support 206.

After the reactor 100 into which a sample has been injected is completely installed, the user may close the door 202, and start a test. Details about a test process will be described below with reference to FIG. 10.

A test apparatus 200 as shown in FIG. 9 may be used to test the disk type reactor 100 as shown in FIG. 4. Referring to FIG. 9, the reactor 100 may include a tray 202 on which the disk type reactor 100 can be rested. After a sample is injected through the inlet hole 121, and then the reactor 100 is rested on the tray 202 of the test apparatus 200, the reactor 100 may be inserted to the inside of a main body 207 of the test apparatus 200 together with the tray 202.

Figure 10:
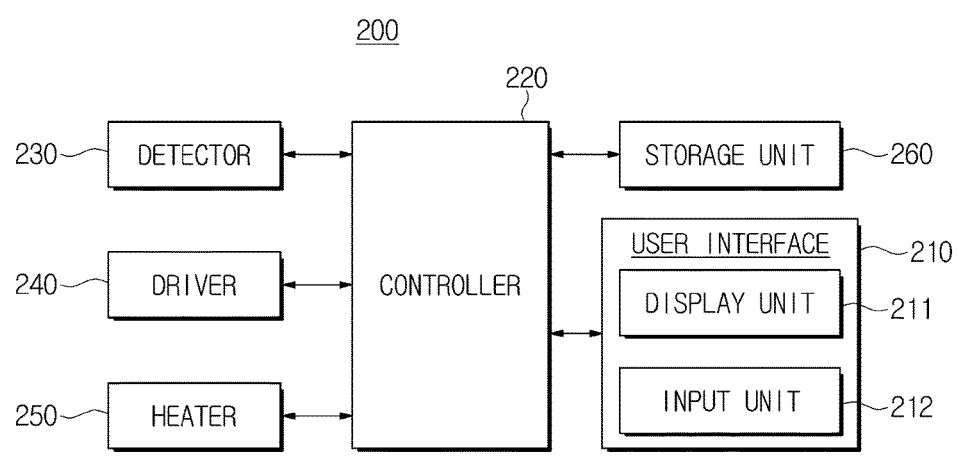
FIGS. 10 and 11 are control block diagrams of a test apparatus, according to an exemplary embodiment.
Figure 11:
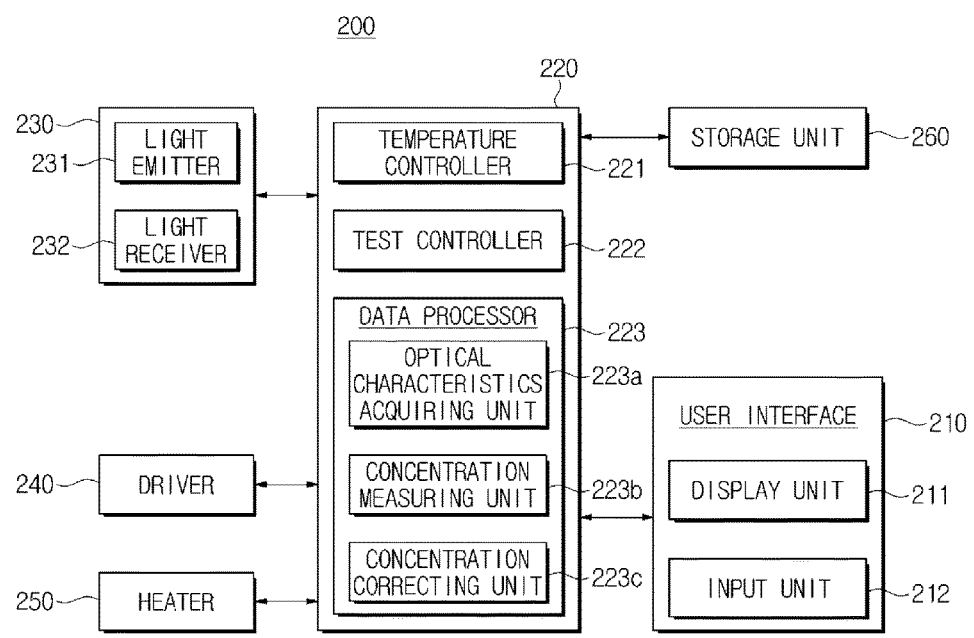

FIGS. 10 and 11 are control block diagrams of a test apparatus, according to an exemplary embodiment. Hereinafter, operations of a test apparatus 200 according to an exemplary embodiment will be described in detail with reference to FIGS. 8, 9, 10, and 11.

Referring to FIG. 10, the test apparatus 200 may include: a user interface 210 that includes a display unit (also referred to herein as a "display device" and/or a "display") 211 configured to provide various information to a user and an input unit (also referred to herein as an "input device") 212 configured to receive control commands from a user; a controller 220 configured to control overall operations of the test apparatus 200; a detector 230 configured to detect a reaction that occurs in a reactor 200 inserted into the test apparatus 200; a driver 240 configured to drive various mechanical components of the test apparatus 200; a heater 250 configured to adjust the internal temperature of the test apparatus 200; and a storage unit (also referred to herein as a "storage device" and/or as a "storage") 260 configured to store various data that is useful for a performance of a test.

The display unit 211 may include any one of various kinds of displays, such as a Light Emission Diode (LED) display, an Organic Light Emission Diode (OLED) display, a Liquid Crystal Display (LCD), a Plasma Display Panel (PDP), and a Cathode Ray Tube (CRT) display.

The input unit 212 may be implemented as a hard-key or a touch panel. For example, a touch panel may be mounted on the front part of the display unit 211 to implement a touch screen, and a power button may be implemented as a hard-key. Accordingly, after the test apparatus 200 is powered on, a user may contact the touch screen in order to input a control command.

The controller 220 may control a test process that is performed on the reactor 100, and process data is acquired by the detector 230 in order to perform concentration measurement and concentration correction/adjustment.

If a reaction that occurs in the reactor 100 involves a change in color, the detector 230 may detect a change in color that occurs in the reactor 100, and transfer the result of the detection to the controller 220.

The driver 240 may include elements, such as a motor or a gear, that can transfer power, and transfer power to a component that needs to move in the test apparatus 200. For example, the driver 240 may generate power needed for any of opening/closing the door 201, causing a pressing unit 205 to press the inlet hole 121, pushing in/drawing out the tray 202, rotating the reactor 100, and/or moving the detector 230, and transfer the generated power to the corresponding component.

The heater 250 may heat the test apparatus 200 such that the internal temperature of the test apparatus 200 reaches an appropriate temperature for a particular test. The heater 250 may further include a cooling function for a test that should be performed at a low temperature.

The storage unit 260 may store any of data for a test process, data for concentration measurement, and data for concentration correction/adjustment, and also may store the results of a test for a predetermined time period.

FIG. 11 is a detailed view of the control block diagram of the test apparatus 200 shown in FIG. 10. Hereinafter, a test process of testing the reactor 200, which is performed by the test apparatus 200, will be described in detail with reference to FIG. 11. However, the test apparatus shown in FIG. 11 is only exemplary, and the configuration of the test apparatus 200 is not limited to the configuration of FIG. 11.

If the door 201 is opened or the tray 202 is drawn out by the driver 240, the reactor 100 can be inserted into the groove 204 or rested on the tray 202. After the door 201 is closed or the tray 202 is pushed in the main body 207, a test process may start inside the main body 207.

The temperature controller 221 may control the heater 250 to adjust the internal temperature of the main body 207 to an appropriate temperature for a particular test. The internal temperature of the main body 207 may be adjusted through pre-heating before the reactor 100 is inserted into the main body 207, or after the reactor 100 is inserted into the main body 207. Further, an appropriate temperature for test may have been set in advance to a default value, or may be set to a predetermined value according to a kind of test or according to a kind of a reagent or a sample contained in the reactor 100.

The test controller 222 may control overall test operations that are performed by the test apparatus 200. If the detector 230 measures optical characteristics, the test controller 222 may control a light emitter 231 to emit an appropriate wavelength of light according to a kind of test, and if the reactor 100 is a disk type, the test controller 222 may control a rotation timing, rotation speed, etc. of the reactor 100 according to a kind of test that is performed by the reactor 100.

For example, information about a kind of test that is performed on the reactor 100 or information about a wavelength of the light emitter 231 may be acquired from a tag attached on the reactor 100. For example, the tag may be attached on the surface of the reactor 100. The tag may include at least one from among a barcode, a two-dimensional (2D) code such as a Quick Response (QR) code, a Radio-Frequency IDentification (RFID) tag, a Near-Field Communication (NFC) tag, and a Bluetooth tag.

If the tag is a 2D code, the light emitter 231 and a light receiver 232 of the detector 230 may scan the 2D code, and read out the 2D code. If the tag is not a 2D code, the test apparatus 200 may include a RFID reader configured to read out RFID tags, a NFC reader configured to read out NFC tags, and/or a Bluetooth reader configured to read out Bluetooth tags.

If the reactor 100 that includes the target material detecting chamber 125-1 and the interfering material detecting chamber 125-2 as shown in FIG. 6 is inserted into the test apparatus 200, the test controller 222 may control the light emitter 231 to irradiate light of a wavelength selected from a wavelength range between 300 nm and 900 nm to the target material detecting chamber 125-1, and to irradiate light of a wavelength selected from a wavelength range between 300 nm and 600 nm to the interfering material detecting chamber 125-2.

Further, the test controller 222 may distinguish optical characteristics acquired by irradiating light of a sub wavelength, from optical characteristics acquired by irradiating light of a main wavelength. The main wavelength, which is specific to a material to be detected, may include a wavelength that the corresponding material can absorb with the highest absorbance, a wavelength that a material produced by a reaction of the corresponding material with a reagent can absorb with the highest absorbance, or a wavelength that a reaction product produced by a reaction accelerated by the corresponding material can absorb with the highest absorbance. The sub wavelength may be used to correct and/or adjust optical characteristics acquired with respect to the main wavelength. When optical characteristics are acquired with respect to the target material detecting chamber 125-1, a main wavelength and a sub wavelength may be selected from a wavelength range between 300 nm and 900 nm, and when optical characteristics are acquired with respect to the interfering material detecting chamber 125-2, a main wavelength and a sub wavelength may be selected from a wavelength range between 300 nm and 600 nm.

For example, an optical density acquired by irradiating light having a wavelength of 810 nm to the target material detecting chamber 125-1 may be distinguished from an optical density acquired by irradiating light having a wavelength of 405 nm to the target material detecting chamber 125-1. Also, an optical density acquired by irradiating light having a wavelength of 535 nm to the interfering material detecting chamber 125-2 may be distinguished from an optical density acquired by irradiating light having a wavelength of 405 nm to the interfering material detecting chamber 125-2.

The light receiver 232 may detect light that has been irradiated from the light emitter 231 and then has propagated through or been reflected from the chamber 125-1 or 125-2. For example, the light emitter 231 may include a lightemitting diode (LED) light source, and the light receiver 232 may include a photodiode or a photodiode array arranged with a plurality of photodiodes.

If the light receiver 232 detects light that has propagated through the chamber 125-1 or 125-2, the light receiver 232 may convert the detected light into an electrical signal that corresponds to an amount of the light, and the data processor 223 may acquire information from data output from the light receiver 232. The data output from the light receiver 232 may be in an analog format or in a digital format.

An optical characteristics acquiring unit 223a may be configured to acquire data about optical densities with respect to the target material detecting chamber 125-1 and the interfering material detecting chamber 125-2 from data output from the light receiver 232. The optical density with respect to the target material detecting chamber 125-1 represents the optical characteristics of a reaction product produced by a reaction of the first reagent with the sample, and the optical density with respect to the interfering material detecting chamber 125-2 represents the optical characteristics of a reaction product produced by a reaction of the second reagent with the sample.

A concentration measuring unit 223b may be configured to measure a concentration of the target material by using the data about the optical density with respect to the target material detecting chamber 125-1, and to measure a concentration of the interfering material by using the data about the optical density with respect to the interfering material detecting chamber 125-2. For example, the concentration measuring unit 223b may store a calibration curve that represents a correlation between optical densities and material concentrations in advance, and apply an acquired optical density to the calibration curve in order to measure a concentration of the corresponding material.

A concentration correcting unit 223c may be configured to correct and/or adjust a measurement of a concentration of a target material by using a concentration of an interfering material. For example, the concentration correcting unit 223c may correct and/or adjust a measurement of a concentration of a target material according to Equation (3), below.

$$C_{TF}=C_{TM}+K \times C_I, \quad (3)$$

where $C_{TF}$ is a final concentration of a target material, $C_{TM}$ is a measured concentration of the target material, K is a factor that corresponds to a degree of influence by which an interfering material influences the concentration of the target material, and $C_I$ is a measured concentration of the interfering material. A value and sign of the K factor may be determined by performing an experiment or simulation. For example, a value and sign of the K factor having the most excellent correlativity may be determined by a result of an experiment or simulation, and the determined value and sign of the K factor may be stored in the storage unit 260 to be applied to tests to be performed later. In addition, the stored K factor can be updated.

If two kinds of interfering materials exist, a concentration of a target material may be corrected and/or adjusted according to Equation (4), below.

$$C_{TF}=C_{TM}+K_1 \times C_{I1}+K_2 \times C_{I2}, \quad (4)$$

where $K_1$ is a first factor that corresponds to a degree of influence by which a first material influences the concentration of the target material, $C_{I1}$ is a measured concentration of the first material, $K_2$ is a second factor that corresponds to a degree of influence by which a second material influences the concentration of the target material, and $C_{I2}$ is a measured concentration of the second material. Likewise, values and signs of the $K_1$ factor and the $K_2$ factor may be determined by performing an experiment or simulation.

The final concentration of the target material acquired by the concentration correcting unit 223c may be displayed on a display unit 211 so that the user can check the final concentration of the target material via the display unit 211.

Further, the controller 220 may include a memory that is configured to store a program for executing the above-described operations, and a processor that is configured to execute the program stored in the memory. Components included in the controller 220 may share a processor, or may include their own processors.

By testing the reactor 100 using the test apparatus 200 as described above, the influence of an interfering material with respect to a concentration of a target material can be minimized so that an accurate measurement of the concentration of the target material can be acquired. For example, when the reactor 100 and the test apparatus 200 are applied to perform a clinical chemical test of detecting a concentration of calcium ions $Ca^{2+}$ included in a body sample, the influence of amylase with respect to a measured concentration of calcium ions $Ca^{2+}$ can be excluded although a large amount of amylase is included in the body sample, thereby acquiring an accurate measurement of the concentration of calcium ions $Ca^{2+}$. Even when pretreatment of diluting a sample before injecting the sample into the reactor 100 is not performed, the influence of an interfering material can be reduced.

Figure 12:
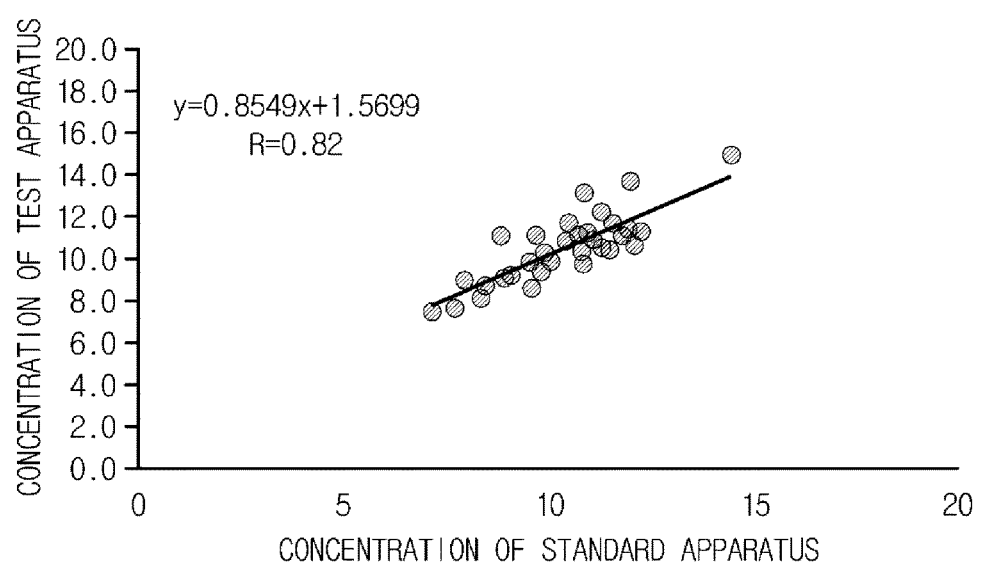
FIG. 12 is a graph showing correlation of results obtained when a reactor according to the related art is tested by a test apparatus according to the related art.
Figure 13:
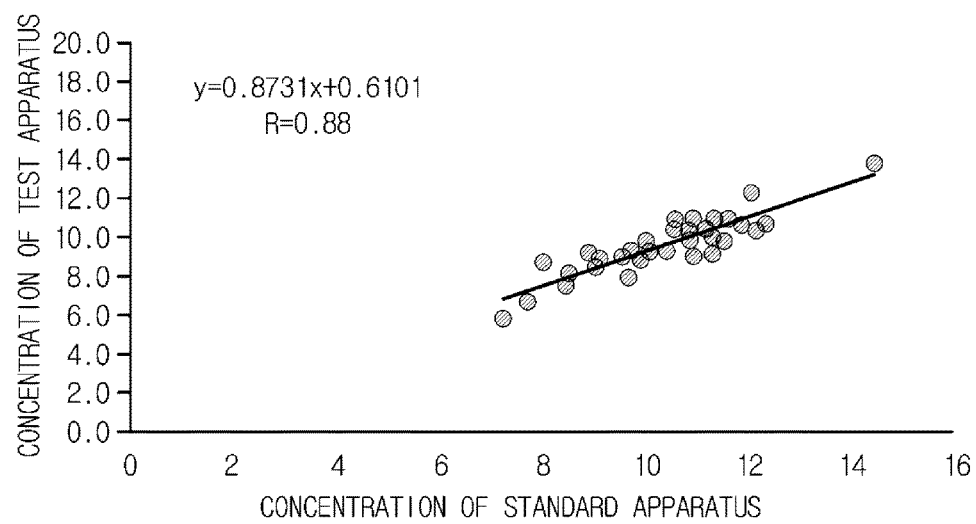
FIG. 13 is a graph showing correlation of results obtained when a reactor according to an exemplary embodiment is tested by a test apparatus according to an exemplary embodiment.

FIG. 12 is a graph showing a correlation of results obtained when a reactor according to the related art is tested by using a test apparatus according to the related art, and FIG. 13 is a graph showing a correlation of results obtained when a reactor according to an exemplary embodiment is tested by using a test apparatus according to an exemplary embodiment.

Correlation is an index that corresponds to a correlation of test results between a standard apparatus and an apparatus that is subject to performance evaluation, and can evaluate accuracy indirectly. Correlation can be represented by a correlation coefficient R, and as the absolute value of the correlation coefficient R is closer to "1", the higher accuracy can be determined.

In experiments designed to acquire correlation as shown in FIGS. 12 and 13, a concentration of calcium ions $Ca^{2+}$ included in a blood sample was measured by using an enzyme method using amylase. In the experiments, a blood sample of 65 μl was used, light having a wavelength of 405 nm was irradiated to a calcium ion detecting chamber (corresponding to a target material detecting chamber), and light having a wavelength of 405 nm was also irradiated to an amylase detecting chamber (corresponding to an interfering material detecting chamber). In order to acquire the correlation of FIG. 13, a K factor value of −25, which was determined by an experiment, was applied to operate the test apparatus 200.

Referring to FIG. 12, when a reactor according to the related art is tested by using a test apparatus according to the related art, in other words, when the influence of amylase is not excluded from a measured concentration of calcium ions $C^{2+}$, a correlation R was measured as 0.82.

Referring to FIG. 13, when a reactor according to an exemplary embodiment is tested by using a test apparatus according to an exemplary embodiment, in other words, when the influence of amylase is excluded from a measured concentration of calcium ions $C^{2+}$, the correlation R was measured as 0.88. The measurement result shows that accuracy was improved compared to when apparatuses according to the related art are used.

Hereinafter, a test method according to an exemplary embodiment of the present disclosure as described above with reference to FIG. 1 will be described in more detail.

In order to perform a test method according to an exemplary embodiment of the present disclosure, the reactor 100 and the test apparatus 200 can be used. Accordingly, the above descriptions and drawings related to the reactor 100 and the test apparatus 200 can be applied to a test method according to the exemplary embodiment.

Figure 14:
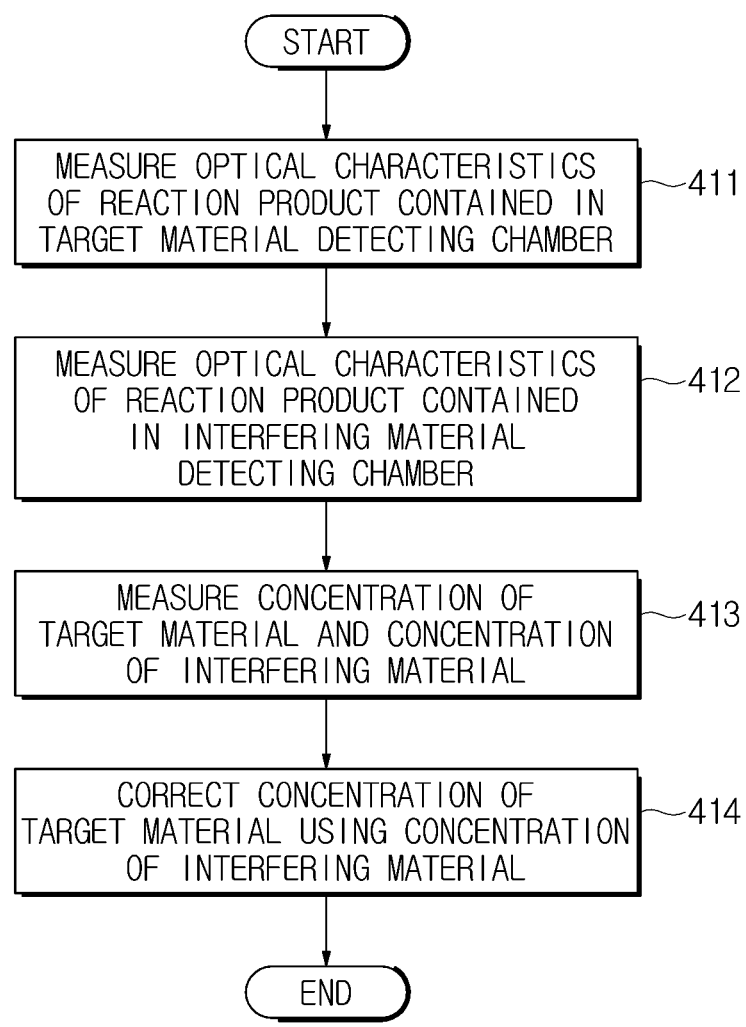
FIG. 14 is a flowchart illustrating a test method, according to an exemplary embodiment.

FIG. 14 is a flowchart illustrating a test method, according to an exemplary embodiment.

Referring to FIG. 14, one or more optical characteristics of a reaction product contained in a target material detecting chamber 125-1 may be measured in operation 411, and one or more optical characteristics of a reaction product contained in an interfering material detecting chamber 125-2 may be measured in operation 412. In FIG. 14, operations 411 and 412 are shown to be performed sequentially in this order, however, operations 411 and 412 may be performed in the reverse order or at the same time.

The target material detecting chamber 125-1 and the interfering material detecting chamber 125-2 have been described above together with the descriptions about the reactor 100. In operation 411, one or more optical characteristics of a reaction product produced when a first reagent that includes a first material that is activated by a target material and at least one reactant that is configured to accelerate a reaction that involves the first material reacts with a sample that includes the target material may be measured. In operation 412, one or more optical characteristics of a reaction product produced when a second reagent that includes the target material and the at least one reactant reacts with the sample may be measured. In order to measure the one or more optical characteristics of the reaction products, light of an appropriate wavelength may be irradiated to the target material detecting chamber 125-1 and the interfering material detecting chamber 125-2 in order to detect light that has propagated through the respective chambers. Herein, the one or more optical characteristics may include an optical density.

Then, a concentration of the target material and a concentration of the interfering material may be measured using the measured one or more optical characteristics, in operation 413.

For example, the measured optical densities may be applied to a calibration curve that corresponds to a correlation between optical densities and concentrations in order to measure a concentration of each material. However, a method of measuring a concentration of each material is not limited to this.

Then, the measurement of the concentration of the target material may be corrected and/or adjust by using the concentration of the interfering material, in operation 414.

In order to correct the measurement of the concentration of the target material, a relation between the concentration of the target material and the concentration of the interfering material may be acquired in advance. The relation between the concentration of the target material and the concentration of the interfering material may be expressed by Equation (3). In Equation (3), the K factor may be acquired based on a result of an experiment or simulation and then stored in the storage unit 160, and the stored K factor may be updated.

Figure 15:
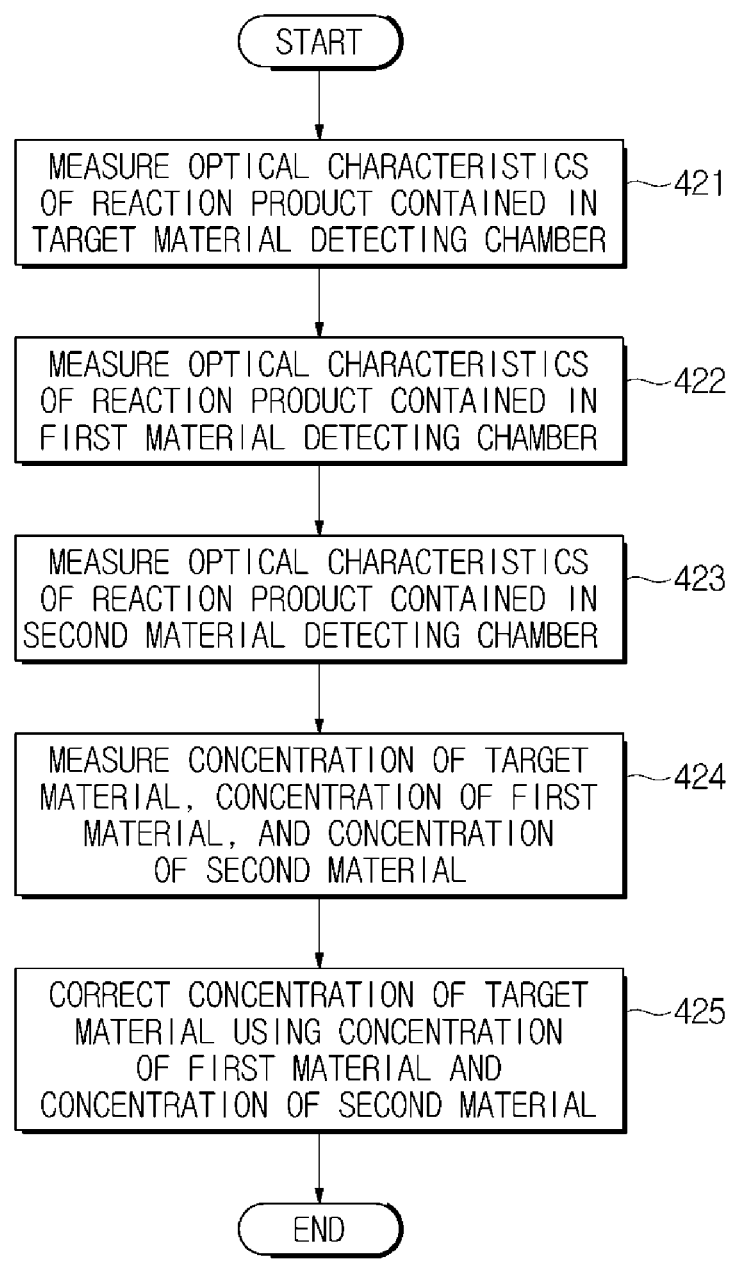
FIG. 15 is a flowchart illustrating a test method when two kinds of interfering materials exist.

FIG. 15 is a flowchart illustrating a test method when two kinds of interfering materials exist.

Referring to FIG. 15, one or more optical characteristics of a reaction product contained in a target material detecting chamber 125-1 may be measured, in operation 421. Then, one or more optical characteristics of a reaction product contained in a first material detecting chamber 125-2 may be measured, in operation 422, and one or more optical characteristics of a reaction product contained in a second material detecting chamber 125-3 may be measured, in operation 423. In FIG. 15, operations 421, 422, and 423 are shown to be performed sequentially in this order, however, operations 421, 422, and 423 may be performed in the reverse order or at the same time.

The target material detecting chamber 125-1, the first material detecting chamber 125-2, and the second material detecting chamber 125-3 have been described above together with the descriptions about the reactor 100. Light of an appropriate wavelength may be irradiated to the target material detecting chamber 125-1, the first material detecting chamber 125-2, and the second material detecting chamber 125-3 in order to detect light that has propagated through the respective chambers, thereby measuring the one or more optical characteristics of each material. The optical characteristics may include an optical density.

Then, a concentration of the target material, a concentration of the first material, and a concentration of the second material may be measured using the one or more measured optical characteristics, in operation 424.

For example, the measured optical densities may be applied to a calibration curve that corresponds to a correlation between optical densities and concentrations in order to measure a concentration of each material. However, a method of measuring a concentration of each material is not limited to this.

Then, the measurement of the concentration of the target material may be corrected and/or adjusted by using the concentration of the first material and the concentration of the second material, in operation 425.

In order to correct the measurement of the concentration of the target material, a relation between the concentration of the target material and the concentrations of the first and second materials may be acquired in advance. For example, the relation between the concentration of the target material and the concentrations of the first and second materials may be expressed by Equation (4). In Equation (4), the $K_1$ factor and the $K_2$ factor may be acquired based on a result of an experiment or simulation and then stored in the storage unit 160, and the stored $K_1$ and $K_2$ factors may be updated.

According to the exemplary embodiments as described above, since the influence of an interfering material with respect to a concentration of a target material can be minimized, an accurate measurement of the concentration of the target material can be acquired. Even when pretreatment of diluting a sample before injecting the sample into the reactor 100 is not performed, the influence of an interfering material can be reduced.

Therefore, the reactor, the test apparatus, and the test method according to the exemplary embodiments can minimize the influence of an interfering material with respect to a concentration of a target material, thereby acquiring an accurate concentration of the target material.

Although a few exemplary embodiments have been shown and described, it will be appreciated by those of skill in the art that changes may be made in these exemplary embodiments without departing from the principles and spirit of the present inventive concept, the scope of which is defined in the claims and their equivalents.

What is claimed is:

1. A test apparatus for measuring a concentration of a target material included in a sample, comprising:
 a detector comprising a light emitter and a light receiver; and
 a controller programmed to measure a concentration of the target material,
 wherein the controller is programmed to control the light emitter to radiate light of a first predetermined wavelength to a target material detecting chamber containing a first reagent that includes a first material that is activated by the target material, and a first material detecting chamber containing a second reagent that includes the target material, and to control the light receiver to detect light that has propagated through or been reflected from the target material detecting chamber and the first material detecting chamber, and
 wherein the controller is further programmed to measure a concentration of the first material based on at least one output signal provided by the detector, and to adjust the measurement of the concentration of the target material based on the measured concentration of the first material.

2. The test apparatus according to claim 1, further comprising a storage configured to store a factor that corresponds to a degree of influence by which the concentration of the first material included in the sample influences the measurement of the concentration of the target material.

3. The test apparatus according to claim 1, wherein the controller is further programmed to measure the concentration of the target material based on a first output signal provided by the detector with respect to the target material detecting chamber, and to measure the concentration of the first material based on a second output signal provided by the detector with respect to the first material detecting chamber.

4. The test apparatus according to claim 2, wherein the factor includes a negative sign or a positive sign, and
 the controller is further programmed to adjust the measurement of the concentration of the target material by adding a value obtained by applying the factor to the measured concentration of the first material to the measured concentration of the target material.

5. The test apparatus according to claim 1, wherein each of the first reagent and the second reagent further includes a second material that is configured for activating the first material, and
 the detector is further programmed to radiate light of a second predetermined wavelength to a second material detecting chamber containing a third reagent that includes the target material and the first material, and to detect light that has propagated through or been reflected from the second material detecting chamber.

6. The test apparatus according to claim 5, wherein the controller is further programmed to measure a concentration of the second material based on a third output signal provided by the detector with respect to the second material detecting chamber.

7. The test apparatus according to claim 6, wherein the controller is further programmed to adjust the measurement of the concentration of the target material based on the measured concentration of the first material and the measured concentration of the second material.

8. The test apparatus according to claim 7, further comprising a storage configured to store a first factor that corresponds to a first degree of influence by which the concentration of the first material included in the sample influences the measured concentration of the target material, and a second factor that corresponds to a second degree of influence by which the concentration of the second material influences the measured concentration of the target material.

9. The test apparatus according to claim 8, wherein each of the first factor and the second factor has a negative sign or a positive sign, and
 the controller is further programmed to adjust the measurement of the concentration of the target material by adding a first value obtained by applying the first factor to the measured concentration of the first material and a second value obtained by applying the second factor to the measured concentration of the second material to the measured concentration of the target material.

* * * * *